US00PP11646P

United States Patent [19]

Abell

[11] Patent Number: Plant 11,646

[45] Date of Patent: Nov. 21, 2000

[54] BRACHYCOME PLANT NAMED 'CITY LIGHTS'

[75] Inventor: Peter George Abell, Blaxland, Australia

[73] Assignee: University of Sydney Plant Breeding Institute, Coffitty, Coffitty, Australia

[21] Appl. No.: 09/195,599

[22] Filed: Nov. 19, 1998

[51] Int. Cl.[7] ..... A01H 5/00

[52] U.S. Cl. ..... Plt./263

[58] Field of Search ..... Plt./263

[56] References Cited

U.S. PATENT DOCUMENTS

P.P. 10,192 1/1998 McAllister ..... Plt./263

*Primary Examiner*—Howard J. Locker
*Assistant Examiner*—Wendy A Baker
*Attorney, Agent, or Firm*—C. A. Whealy

[57] ABSTRACT

A new and distinct cultivar of Brachycome plant named 'City Lights', characterized by its compact and outwardly spreading growth habit; very freely branching plant habit, plants do not require pinching; numerous and showy inflorescences with lavender ray florets that are about 2.5 cm in diameter; and long peduncles that hold inflorescences above or beyond the foliage.

1 Drawing Sheet

BACKGROUND OF THE INVENTION

The present invention relates to a new and distinct cultivar of Brachycome plant, botanically known as Brachycome hybrid and referred to by the cultivar name City Lights.

The new Brachycome is a product of a planned breeding program conducted by the Inventor in Cobbitty, New South Wales, Australia. The objective of the program is to create new compact Brachycome cultivars that flower early, are easy to propagate, have uniform plant habit, and have large inflorescences with attractive ray floret color.

The new Brachycome originated from a cross by the Inventor in 1995 of the *Brachycome multifida* cultivar Billabong Bright Eyes (disclosed in U.S. Plant Pat. No. 10,192), as the female, or seed, parent with an unidentified selection of *Brachycome segmentosa* as the male, or pollen, parent. The cultivar City Lights was discovered and selected by the Inventor in 1996 as a flowering plant within the progeny of the stated cross in a controlled environment in Cobbitty, New South Wales, Australia.

Asexual reproduction of the new Brachycome by terminal cuttings taken in a controlled environment in Cobbitty, New South Wales, Australia, has shown that the unique features of this new Brachycome are stable and are reproduced true to type in successive generations.

SUMMARY OF THE INVENTION

The new Brachycome has not been observed under all possible environmental conditions. The phenotype may vary somewhat with variations in environment such as temperature, saylength and light intensity, without, however, any variance in genotype.

The following characteristics have been repeatedly observed and are determined to be basic characteristics of 'City Lights' and distinguish 'City Lights' as a new and distinct cultivar:

1. Compact and outwardly spreading growth habit.
2. Very freely branching plant habit, plants do not require pinching.
3. Numerous and showy inflorescences with lavender ray florets that are about 2.5 cm in diameter.
4. Long peduncles that hold inflorescences above or beyond the foliage.

Compared to plants of the female parent, the cultivar Billabong Bright Eyes, plants of the new Brachycome are larger, more vigorous and have larger inflorescences.

Compared to plants of the male parent, an unidentified selection of *Brachycome segmentosa*, plants of the new Brachycome are denser, more spreading and have finer foliage. In addition, ray floret color of plants of the male parent is white.

Plants of the new Brachycome can be compared to nonpatented species *Brachycome multifida*, common name Hawkesbury River Daisy. However, in side-by-side comparisons conducted in Cobbitty, New South Wales, Australia, plants of the new Brachycome differ from plants of Hawkesbury River Daisy in the following characteristics:

1. Plants of the new Brachycome have lighter and brighter green foliage color than plants of Hawkesbury River Daisy.
2. Plants of the new Brachycome have larger inflorescences than plants of Hawkesbury River Daisy.
3. Ray floret color of plants of the new Brachycome is paler than ray floret color of plants of Hawkesbury River Daisy.
4. Plants of the new Brachycome have longer peduncles than plants of Hawkesbury River Daisy.

BRIEF DESCRIPTION OF THE PHOTOGRAPHS

The accompanying colored photogarphs illustrate the overall appearance of the new Brachycome, showing the colors as true as it is reasonably possible to obtain in colored reproductions of this type. Colors in the photographs may differ slightly from the color values cited in the Detailed Botanical Description which accurately describe the actual colors of the new Brachycome.

The photograph at the top of the sheet comprises a top perspective view of a typical potted plant of 'City Lights'.

The photograph at the bottom of the sheet comprises a close-up view of typical developing inflorescences of 'City Lights' from bud stage (left) to fully opened inflorescence (right).

DETAILED BOTANICAL DESCRIPTION

The following observations, measurements, values, and comparisons describe plants grown in Bonsall, Calif., under outdoor full-sun conditions with day temperatures ranging from 18 to 35° C., night temperatures ranging from 13 to 18° C. Color references are made to The Royal Horitcultural Society Colour Chart except where general terms of ordinary dictionary significance are used.

Botanical classification: Brachycome hybrid cultivar City Lights.

Parentage:

*Male or pollen parent.*—Unidentified selection of *Brachycome segmentosa.*

*Female or seed parent.*—*Brachycome multifida* cultivar Billabong Bright Eyes, disclosed in U.S. Plant Pat. No. 10,192.

Propagation:

*Type.*—By cuttings.

*Time to initiate roots.*—Summer: About 10 days at temperatures of 25° C. Winter: About 15 days at temperatures of 20° C.

*Time to develop roots.*—Summer: About 15 days at temperatures at 25° C. Winter: About 20 days at temperatures of 20° C.

*Rooting habit.*—Fine, fibrous and freely branching.

Plant description:

*General appearance.*—Compact and outwardly spreading; rounded and mounding; full and dense; herbaceous plant with long peduncles that hold inflorescences above and beyond the foliage. Suitable for 12.5 to 20-cm containers and hanging baskets. To produce a 12.5-cm finished flowering plant from rooted cuttings, about 8 to 12 weeks are required depending on temperature and light level.

*Plant height.*—About 16 cm from soil level to top of inflorescences.

*Plant diameter or spread.*—About 26 cm.

*Branching.*—Very freely branching, pinching is usually not required.

*Growth rate/vigor.*—Vigorous.

*Stem description.*—Quantity of lateral branches: Typically about 15 per plant with numerous secondary and tertiary branches. Lateral branch length: About 30 cm. Lateral branch diameter: About 2 mm. Internode length: About 1 to 2 cm. Texture: Glabrous. Color: 144C.

*Foliage description.*—Arrangement: Alternate. Quantity: About 250 per lateral branch. Shape: Single leaves that are deeply dissected; typical with seven leaf segments that are narrowly obovate; apex, acute to dentate; base, attenuate. Length: About 2.2 cm. Width: About 1 cm. Margin: Entire to slightly dentate. Texture: Smooth. Petiole length: About 5 mm. Petiole diameter: About 1 mm. Color: Young leaves, upper surface: 137A. Young leaves, lower surface: 137C. Fully expanded leaves, upper surface: 137A. Fully expanded leaves, lower surface; 137C. Petiole: 137C.

Flowering description:

*Inflorescence.*—Single daisy-type composite inflorescence form. Florets arranged acropetally on a capitulum. Inflorescences held above and beyond the foliage on long peduncles. Inflorescences maintain good color and substance for about 2 to 3 weeks. Inflorescences persistent.

*Natural flowering season.*—Natural flowering season is spring to fall; flowering continuous during this period.

*Quantity of inflorescences.*—Floriferous with typically about 17 open inflorescences and buds per lateral stem; more than 200 open inflorescences and buds per plant.

*Inflorescence diameter.*—About 2.5 cm.

*Inflorescence depth* (*height*).—About 6 mm.

*Disc diameter.*—About 7 mm.

*Inflorescence aspect.*—Flat.

*Rate of inflorescence opening.*—About 5 to 10 days depending on temperature.

*Fragrance.*—None detected.

*Inflorescence bud* (*showing color*).—Shape: Rounded to oblong. Length: About 8 mm. Diameter: About 6 mm. Color: 85B.

*Ray florets.*—Quantity: One whorl of about 36 florets per inflorescence. Shape: Narrowly oblong. Apex: Rounded or slightly notched. Base: Attenuate. Margin: Entire. Aspect: Flat. Length: About 1.2 cm. Width: About 3 mm. Texture: Smooth. Color: When opening, upper surface: 91A. When opening, lower surface: 91C. Mature, upper surface: 85A, with further development, floret color fades to 85B to 85C. Mature, lower surface: 85C to 85D.

*Disc florets.*—Shape: Tubular with 5-lobed corolla. Length: About 5 mm. Width: About 1 mm. Color: Immature: 1A. Mature: 2A. Number of disc florets per inflorescence: About 39.

*Peduncle.*—Length: Terminal peduncle: About 7.5 cm. Fourth peduncle: About 5 cm. Strength: Flexible, moderate strength. Angle: Acute. Texture: Smooth. Color: 144A; occasional anthocyanin.

*Involucral bracts*—Arrangement: Imbricate, two whorls. Quantity: About 12 per inflorescence. Shape: Mostly elliptic. Apex: Broadly acute. Margin: Entire, membranous giving a translucent fringed appearance. Texture: Smooth. Color: Upper surface: 138C. Lower surface: 138A.

*Androecium.*—Stamen number: Five per disc floret. Anther shape: Oblong. Anther size: About 1 mm. Anther color: 2A. Amount of pollen: Scarce. Pollen color: 2A.

*Gynoecium.*—Pistil number: One per floret. Stigma shape: Bilobed. Pistil length: About 3 mm. Style color: 4A. Stigma color: 4A. Ovary color: 145C, Disease resistance: Disease resistance to pathogens common to Brachycome has not been observed, Seed production: Seed production has not been observed.

It is claimed:

1. A new and distinct cultivar of Brachycome plant named 'City Lights', as illustrated and described.

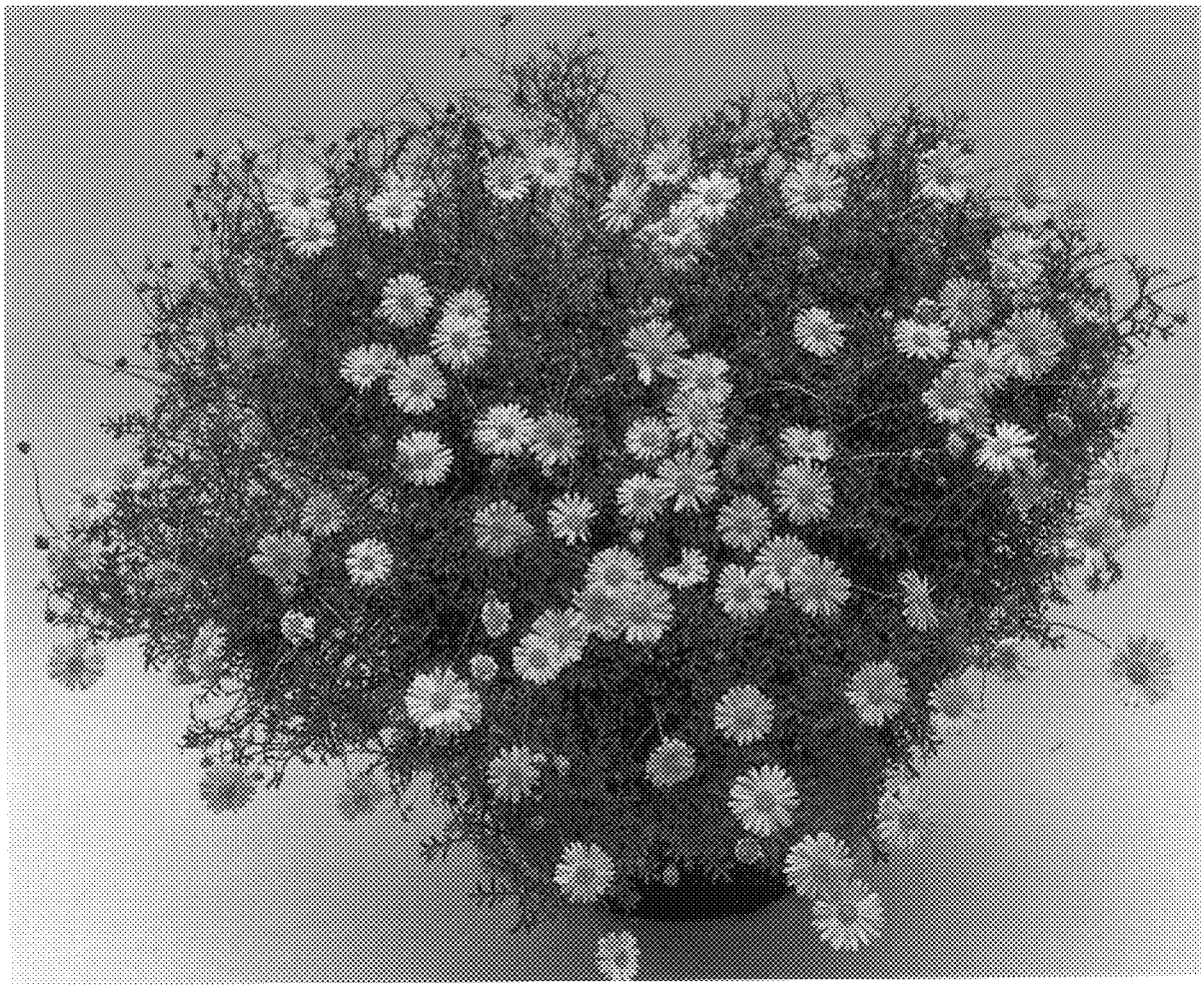
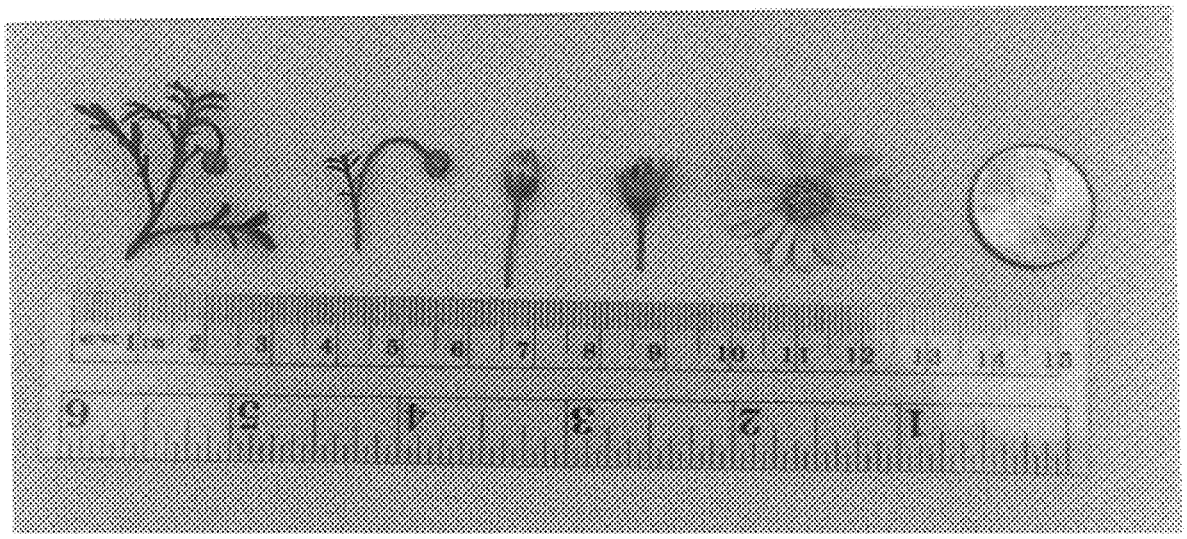

* * * * *